(12) United States Patent
De Chillou

(10) Patent No.: US 10,891,728 B2
(45) Date of Patent: Jan. 12, 2021

(54) METHOD AND SYSTEM FOR IDENTIFYING AN ISTHMUS IN A THREE-DIMENSIONAL MAP

(71) Applicants: UNIVERSITE DE LORRAINE, Nancy (FR); CENTRE HOSPITALIER REGIONAL DE NANCY, Nancy (FR)

(72) Inventor: Christian De Chillou, Marly (FR)

(73) Assignees: UNIVERSITE DE LORRAINE, Nancy (FR); CENTRE HOSPITALIER REGIONAL DE NANCY, Nancy (FR)

( * ) Notice: Subject to any disclaimer, the term of this patent is extended or adjusted under 35 U.S.C. 154(b) by 347 days.

(21) Appl. No.: 15/564,033

(22) PCT Filed: Apr. 1, 2016

(86) PCT No.: PCT/EP2016/057237
§ 371 (c)(1),
(2) Date: Oct. 3, 2017

(87) PCT Pub. No.: WO2016/156578
PCT Pub. Date: Oct. 6, 2016

(65) Prior Publication Data
US 2018/0089825 A1 Mar. 29, 2018

(30) Foreign Application Priority Data
Apr. 3, 2015 (FR) ...................... 15 52901

(51) Int. Cl.
*A61B 5/04* (2006.01)
*G06T 7/00* (2017.01)
(Continued)

(52) U.S. Cl.
CPC .......... *G06T 7/0012* (2013.01); *A61B 5/0044* (2013.01); *A61B 5/04012* (2013.01);
(Continued)

(58) Field of Classification Search
CPC .............. A61B 5/0044; A61B 5/04012; A61B 5/04525; A61B 5/0472; A61B 5/055;
(Continued)

(56) References Cited

U.S. PATENT DOCUMENTS 10,149,626 B1 * 12/2018 Boveja ............... A61B 5/04012

OTHER PUBLICATIONS

French Search Report from French Patent Application No. 1552901, dated Jan. 21, 2016.
(Continued)

*Primary Examiner* — Amanda K Hulbert
(74) *Attorney, Agent, or Firm* — Greer, Burns & Crain, Ltd.

(57) ABSTRACT

A method is provided for identifying an isthmus in a three-dimensional map of a cardiac cavity by means of a processing unit configured to perform the following steps: a) correlation between a set of stimulated points of the cardiac cavity, each stimulated point being represented by a set of signals that are obtained following surface electrocardiography (ECG), excluding ventricular tachycardia; b) identification of a watershed line on the basis of the above correlation results and of the 3D coordinates of the stimulated points in the 3D map; and c) determination of the isthmus based on a 3D corridor substantially transverse to the watershed line.

10 Claims, 3 Drawing Sheets

(51) Int. Cl.

| | |
|---|---|
| *A61B 5/0452* | (2006.01) |
| *A61B 5/0472* | (2006.01) |
| *A61B 5/00* | (2006.01) |
| *G06K 9/00* | (2006.01) |
| *A61B 5/055* | (2006.01) |
| *G06T 7/187* | (2017.01) |
| *G06T 7/11* | (2017.01) |
| *G01R 33/32* | (2006.01) |

(52) U.S. Cl.
CPC ........ *A61B 5/0472* (2013.01); *A61B 5/04525* (2013.01); *A61B 5/055* (2013.01); *A61B 5/489* (2013.01); *G01R 33/323* (2013.01); *G06K 9/0055* (2013.01); *G06K 9/0057* (2013.01); *G06K 9/00201* (2013.01); *G06T 7/11* (2017.01); *G06T 7/187* (2017.01); *G06T 2207/20152* (2013.01); *G06T 2207/30048* (2013.01)

(58) Field of Classification Search
CPC .. A61B 5/489; G01R 33/323; G06K 9/00201; G06K 9/0055; G06K 9/0057; G06T 2207/20152; G06T 2207/30048; G06T 7/0012; G06T 7/11; G06T 7/187
See application file for complete search history.

(56) References Cited

OTHER PUBLICATIONS

International Search Report from International Patent Application No. PCT/EP2016/057237, dated Jun. 16, 2016.
De Chillou, Christian, "Catheter Ablation of Post-Infarct VT Background," (Powerpoint), Institut Lorrain du Coeur et des Vaisseaux—University Hospital Nancy, Jan. 30, 2014, retrieved from the internet <http://sfcardio.fr/sites/default/files /pdf/Chillou-a565.pdf>, pp. 71-95.
De Chillou et al., "Localizing the Critical Isthmus of Postinfarct Ventricular Tachycardia: The Value of Pace-mapping During Sinus Rhythm," Heart Rhythm (2014), 11(2), pp. 175-181.
De Chillou et al., "Showing Up Channels for Postinfarct Ventricular Tachycardia Ablation," PACE (2012), 35(7), pp. 897-904.
Dickfeld et al., "MRI-Guided Ventricular Tachycardia Ablation: Integration of Late Gadolinium-Enhanced 3D Scar in Patients with Implantable Cardioverter-Defibrillators," Circulation, Arrhythmia and Electrophysiology (2011), 4(2), pp. 172-184.
Gerstenfeld et al., "Quantitative Comparison of Spontaneous and Paced 12-Lead Electrocardiogram During Right Ventricular Outflow Tract Ventricular Tachycardia," Journal of the American College of Cardiology (2003), 41(11), pp. 2046-2053.
Moreno et al., "Pacemapping," Indian Pacing and Electrophysiology Journal (2005), 5(1), pp. 35-42.
Stevenson et al., "Interventional Cardiac Electrophysiology: Catheter Ablation for Ventricular Tachycardia," Circulation (2007), 115(21), pp. 2750-2760.

* cited by examiner

METHOD AND SYSTEM FOR IDENTIFYING AN ISTHMUS IN A THREE-DIMENSIONAL MAP

BACKGROUND

The present invention relates to a method and a system for identifying an isthmus in a three-dimensional mapping. It has a particularly useful application in the field of disturbances of the cardiac rhythm, during a ventricular tachycardia for example.

Since the start of the 1990's and the use of radiofrequency energy for endocavitary ablation for rapid rhythm disorders, the indications for ablation have been progressively extended to all rhythm disorders.

In fact, interventional heart rhythm specialists are treating rhythm disorders the mechanism of which is increasingly complex, added to the need for accurate spatial representation of the positioning of the ablation catheter and finally, integration of the spatial and temporal data, in order to identify the arrhythmogenic substrate.

3D mapping systems associated with magnetic resonance imaging (MRI) constitute a very important tool for the interventional heart rhythm specialist. These systems represent a considerable help for identifying the complex arrhythmogenic substrates which require "tailored" ablations for a given patient.

The help provided by these systems involves not only understanding and spatial indexing of the arrhythmogenic substrate, but also the accurate positioning of the ablation catheter. Another element of progress relates to the reduction in X-ray exposure time, both for the patient and also for the electrophysiology team, as these systems do not use X-rays in their clean technology.

In normal function, the atria of the heart impose the heartbeat rhythm on the ventricles. The latter receive blood from the atria and contract in a synchronized fashion in order to eject the blood either to the lungs or to the other organs of the body. Electrical pulses at the level of the atria allow this contraction. Ventricular tachycardia occurs when the electrical pulse originates at the level of the muscle of one of the two ventricles and not from the atria. Ventricular tachycardia (VT) is a rapid arrhythmia, i.e. a very rapid acceleration of the heart above 180 beats per minute for example. The heart can no longer fill; the heart pump then beats while empty. This poor function can degenerate into another arrhythmia, ventricular fibrillation, which can lead to a cardiac arrest if it is not treated rapidly with success.

It is considered that three fundamental mechanisms can be at the origin of ventricular tachycardias:
  diastolic depolarization phenomena,
  focal re-excitation phenomena, and
  reentry phenomena, the latter being the most frequent.

The concept of reentry requires the presence of a slow conduction zone.

Generally, the diagnosis is established using an electrocardiogram (ECG) recorded during ventricular tachycardia.

The purpose of the ECG is to collect simultaneously, on several leads (pairs of electrodes), the overall electrical activity of the heart (cardiac vector): propagation in time and in space.

The leads correspond to the pairs of electrodes present during the recording. Each lead gives a unidirectional image of the cardiac activation vector. This image corresponds to the projection of the vector on the lead. A standard ECG records the cardiac activity on 12 to 18 leads, which divide into two categories:

Peripheral leads and
Precordial leads.

The tracing must comprise the 12 main leads as a minimum, i.e., in order: the three standard leads (I, II, III), the three unipolar limb leads (aVR, aVL, aVF), and the six precordial leads from V1 to V6.

A 12-Lead ECG is a set of 12 curves each having particular shapes such as a bump for a P wave or a rapid variation for a QRS complex.

A QRS complex corresponds to the depolarization of the ventricles. It has an average duration of approximately 0.08 sec.

As regards preventive treatments, an automatic defibrillator can be used implanted in the patient so as to generate electrical pulses in case arrhythmia starts.

A medicinal treatment can also be implemented in order to reduce the number of crises.

Finally, it is possible to carry out radiofrequency ablation when an arrhythmia linked to the reentry mechanism is involved. In this case it is a question of identifying the low conduction zone which will be destroyed by burning so as to create a barrier to the intraventricular circuit forming an arrhythmogenic substrate and containing this low conduction zone. This arrhythmogenic substrate, also called an isthmus, can be determined during an electrophysiological exploration, the patient being in ventricular tachycardia. It can be cauterized and limited by a probe the end of which is heated by a radio frequency current. The examination is helped by a three-dimensional heart mapping system. This technique has good efficacy but the risk of recurrence is not eliminated and as a rule does not allow the implantation of a defibrillator to be dispensed with.

A postinfarct isthmus ablation technique of this type is known, in which surface ECGs are carried out and then compared to a reference ECG recorded during an episode of ventricular tachycardia. Such a technique is described in the document "Localizing the critical isthmus of postinfarct ventricular tachycardia: the value of pace-mapping during sinus rhythm", by Chillou et al, Heart Rhythm; 2014 February; 11(2):175-81.

SUMMARY

A purpose of the present invention is a novel method for rapidly determining the isthmus.

Another purpose of the invention is identifying the isthmus in a completely preventive fashion, even for patients unable to withstand, specifically, a provoked episode of ventricular tachycardia.

At least one of the aforementioned objectives is achieved with a method for identifying an isthmus in three-dimensional mapping of a cardiac cavity, by means of a processing unit configured to carry out the following steps:

a) correlation between a set of stimulated points of the cardiac cavity, each stimulated point being represented by a set of signals obtained following surface electrocardiography (ECG), excluding ventricular tachycardia, in sinus rhythm for example, b) identifying a watershed line based on the above correlation results and the 3D coordinates of the stimulated points in the 3D mapping, c) determining the isthmus based on a 3D corridor substantially transverse to the watershed line.

The invention can relate to a method for identifying a watershed line in three-dimensional mapping of a cardiac cavity, by means of a processing unit configured to carry out the following steps:

a) correlation between a set of stimulated points of the cardiac cavity, each stimulated point being represented by a set of signals obtained following surface electrocardiography (ECG), excluding ventricular tachycardia, in sinus rhythm for example, b) identifying a watershed line based on the above correlation results and the 3D coordinates of the stimulated points in the 3D mapping.

The expression "excluding ventricular tachycardia" is an expression that is clear to a person skilled in the art which means that the ECG is acquired according to a base rhythm which is not ventricular tachycardia (VT). It is known to a person skilled in the art that the rhythm excluding VT can be a sinus rhythm most of the time, but can also be atrial fibrillation, a rhythm electrically controlled by a pacemaker etc.

The watershed line corresponds to abrupt variation in the correlations between near neighbours.

With the method according to the invention, reference electrocardiography, which is generally ventricular tachycardia electrocardiography, is not used, the latter having the drawback of being time-consuming and putting the patient at risk.

Correlation between the different points makes it possible to demonstrate an abrupt geographical variation between correlation levels, this abrupt geographical variation zone corresponding to a zone of very low electrical conduction.

According to the invention, the stimulated points are sites in a patient's heart which are stimulated so as to obtain an electrocardiogram. These points can be chosen at random throughout the entire volume of the cardiac cavity, but they can also be determined methodically.

According to an advantageous characteristic of the invention, prior to step a), a step is carried out to constitute several overlapping volumes in the 3D mapping, these volumes containing the set of stimulated points, step a) being carried out between stimulated points of each of the volumes.

In this way families of points are constituted. In each family calculations are carried out of the correlation coefficient of each point with respect to all the others, or of each point with respect to these near neighbours only. A point can be part of several volumes or families, thus ensuring continuity throughout the cardiac cavity.

According to an advantageous embodiment of the invention, in order to save time during implementation, not all of the cardiac cavity is stimulated equally. According to the invention, at least one iteration of steps a) and b) can preferably be carried out; at each iteration, new stimulated points are added close to the watershed line identified in the preceding iteration. In this way, a maximum correlation coefficient is calculated around the watershed line, which is the zone which allows the isthmus to be precisely identified. The other zones can contain very few stimulated points.

Carrying out the iterations makes it possible to obtain broad identifications initially, becoming increasingly precise; the criterion for stopping the iterations can be the duration, number of points stimulated, or a predetermined number of iterations.

Preferably, said signals can correspond to the 12 leads of a surface ECG.

According to an advantageous embodiment of the invention, the correlation is carried out on QRS complexes originating from said signals.

In this case a first step can be identifying the QRS complexes in the signals. This allows an improvement in the speed of the calculations and as a result the speed of the entire procedure for identifying the isthmus.

In particular, the correlation can be implemented according to the BARD algorithm called "template matching" or correspondence diagram. This method is described in particular in the document "Quantitative Comparison of Spontaneous and Paced 12-Lead Electrocardiogram During Right Ventricular Outflow Tract Ventricular Tachycardia", Gerstenfeld E P et al. J Am Coll Cardiol 2003; 41:2046-53.

This involves comparing the morphology of the 12-Lead ECG complexes. The Bard method defines a numerical calculation making it possible to compare two 12-lead electrocardiograms by objective criteria.

The correlation coefficient CORR is calculated in the usual way. For two completely opposite wave forms the correlation coefficient CORR=−1. For two identical wave forms the correlation coefficient CORR=1. Two wave forms with a similar morphology each containing one-third of the zone of the other have a correlation coefficient CORR=1.

For comparing the multiple wave forms, such as those of the complexes of a 12-lead ECG, the formula is:

$$CORR = \frac{\sum_{lead\,1}^{12}\left[\sum_{i=1}^{n}(X_i - \overline{X})\cdot(Y_i - \overline{Y})\right]}{\sum_{lead\,1}^{12}\left[\sqrt{\sum_{i=1}^{n}(X_i - \overline{X})^2 \cdot \sum_{i=1}^{n}(Y_i - \overline{Y})^2}\right]}$$

where X and Y are vectors of length n representing the two signals to be compared. The correlation coefficient CORR generally varies from −1 for a completely opposite wave form to +1 for identical signals.

According to a characteristic of the invention, step a) comprises moreover a step for identifying groups of stimulated points as a function of the level of correlation between these stimulated points.

The first distribution by family is a geographical distribution only; here the level of the correlation coefficient is used as criterion. Advantageously, groups are identified by displaying on a display screen, with an identical colour, the set of stimulated points of one and the same group. A colour code is determined, making it possible to display a group having a high coefficient of correlation with one another. This can allow easy visual identification of an isthmus.

According to another aspect of the invention, a system is proposed for identifying an isthmus in a three-dimensional mapping of a cardiac cavity, this system comprising:
an electrocardiograph for generating an electrocardiography by stimulating several points of a body, and
a processing unit configured to carry out the following steps:
a) correlation between a set of stimulated points of the cardiac cavity, each stimulated point being represented by a set of signals obtained following surface electrocardiography (ECG), excluding ventricular tachycardia,
b) identifying a watershed line based on the above correlation results and the 3D coordinates of the stimulated points in the 3D mapping,
c) determining the isthmus based on a 3D corridor substantially transverse to the watershed line.

This system can moreover advantageously comprise an ablation catheter.

BRIEF DESCRIPTION OF THE DRAWINGS

Other advantages and characteristics of the invention will become apparent on examination of the detailed description of an embodiment which is in no way limitative, and the attached drawings, in which.

DETAILED DESCRIPTION

In the prior art, it was sometimes necessary to provoke a ventricular tachycardia episode so as to have a reference ECG. This was then compared with other sinus rhythm ECGs (normal heart function). With the present invention, this episode which is sometimes artificially triggered is avoided. In fact, this could be complicated for patients equipped with a permanent pacemaker or defibrillator.

Figure 1:
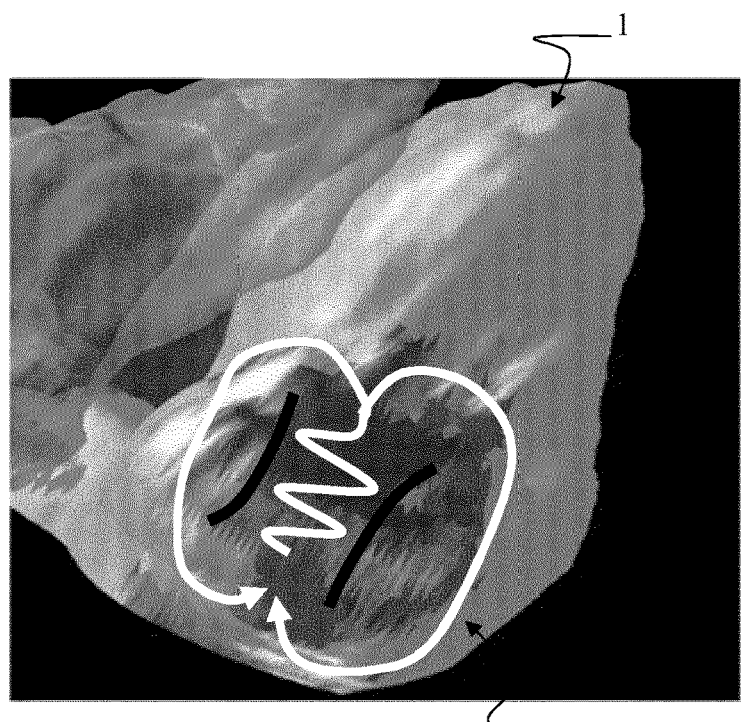
FIG. 1 is a three-dimensional representation of a cardiac cavity with an illustration of an electrical circuit in the case of ventricular tachycardia.

The present invention involves a system of 3D mapping making it possible to have a three-dimensional representation of the heart, as can be seen in FIG. 1. In particular, the left ventricle 1 is distinguished as a whole. This is an amplitude mapping of the left ventricle of a patient presenting with sequelae of an earlier infarctus. The healthy zones appear entirely outside the circuit 2 drawn on the mapping and the infarction sequelae entirely inside this circuit 2.

Figure 2:
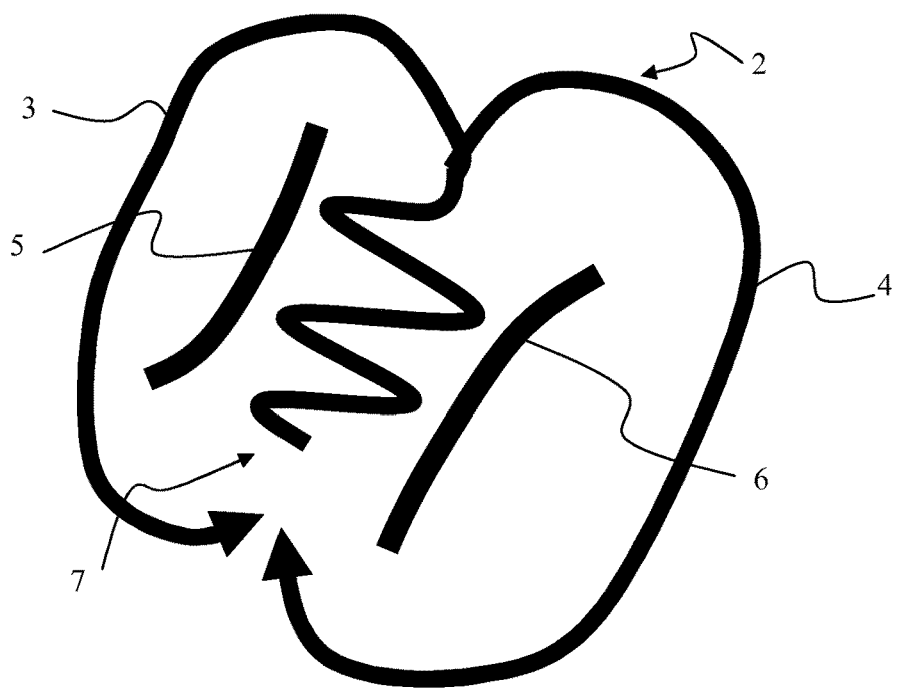
FIG. 2 is a simplified diagrammatic view of the reentry electrical circuit revealing the isthmus to be identified.

The circuit 2 is more clearly shown in FIG. 2. This circuit shows the pathway of a depolarization front during an episode of tachycardia. All the ventricular tachycardias can be represented by a reentry circuit 2 in the form of a double loop forming a figure of eight, the two loops 3 and 4 being the seat of a depolarization front circulating in opposite directions around barriers 5 and 6 delimiting the isthmus. The isthmus is the central zone 7 which forms the arrhythmogenic substrate of the mapped arrhythmia.

Treatment of the ventricular tachycardia amounts to carrying out an ablation of the isthmus. More precisely, a part of the isthmus is burnt away by radiofrequency waves so as to produce a break therein and thus prevent the propagation of the depolarization wave.

The invention is remarkable in particular for the fact that the ablation zone is determined without resorting to a prior ventricular tachycardia ECG.

In order to do this, a catheter is used for stimulating several points of the cardiac cavity for about ten seconds. At each stimulated point, a 12-lead ECG is obtained. FIG. 2 shows a random distribution of these points. A priori the circuit 2 which is represented in FIGS. 2 to 6 is unknown. It is represented simply to aid understanding. The distribution of the points can be random but it can also be obtained in a methodical, in particular predetermined, manner, so as for example to cover a surface or a volume evenly. The distribution can therefore be homogeneous or defined as a function of physiological criteria.

Figure 3:
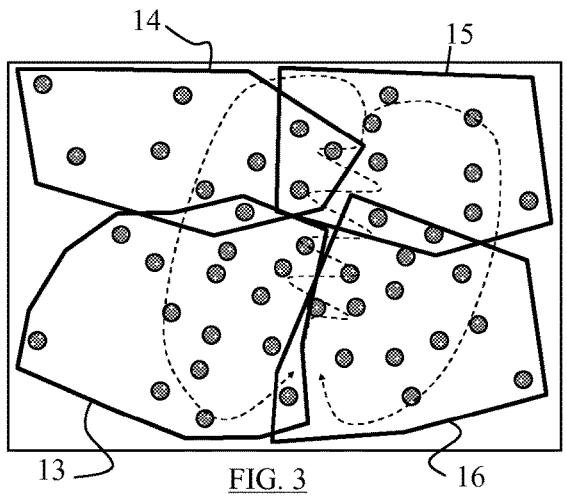
FIGS. 3 to 5 are diagrammatic views of a set of stimulated points in the cardiac cavity, these different figures illustrating different steps of pair correlation between the different stimulated points so as to constitute a density map making it possible to form groups among highly-correlated stimulated points.
Figure 4:
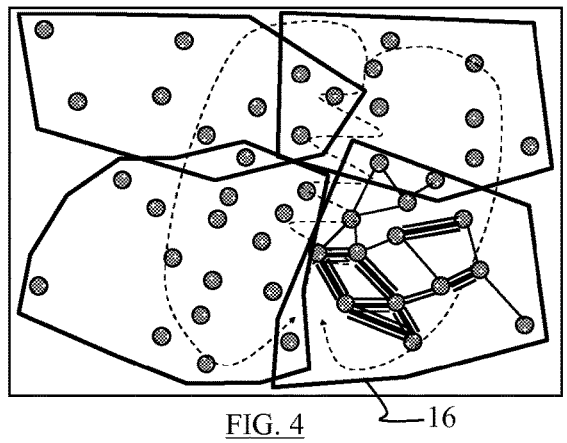

In a second step, several points that are geographically close are grouped together. These groups constituted in this way can overlap so that one point can belong to several groups. Each group is a family of points which are geographically close to each other. In FIG. 3, for example four families 13, 14, 15 and 16 can be seen.

A correlation coefficient is determined for each pair of a family. To this end, the Bard method is used, taking into account the twelve leads associated with each stimulated point. Thus, a mapping of densities is established of the links between different stimulated points, as can be seen very diagrammatically in FIG. 4 with reference to the family 16. In each family, techniques can be utilized making it possible to determine the correlation coefficients step by step, without necessarily calculating this coefficient for all the pairs of the family.

Figure 7:
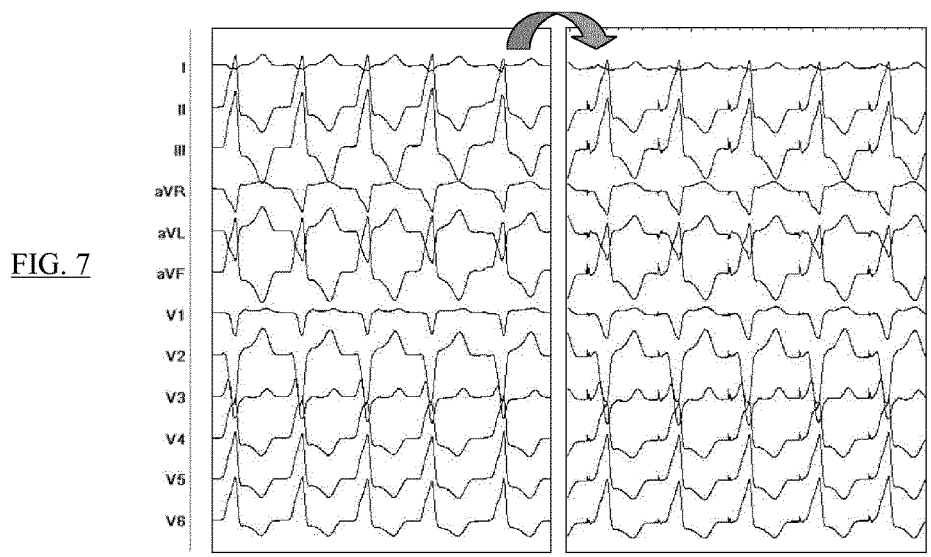
FIG. 7 is a diagrammatic view of two electrocardiograms that are to undergo a correlation operation.

FIG. 7 shows two sets of signals of two electrocardiograms are seen, obtained after stimulation of two points in sinus rhythm. Unlike in the prior art, a reference ECG originating from a prior ventricular tachycardia is not used here. The ECGs are compared with each other, preferably by family or in a general fashion.

Then the points having substantially the same density are identified, i.e. the points which are strongly linked together independently of the families constituted above. In this way groups of points that are strongly linked together as seen in FIG. 5 for the groups 17 and 18.

Figure 5:
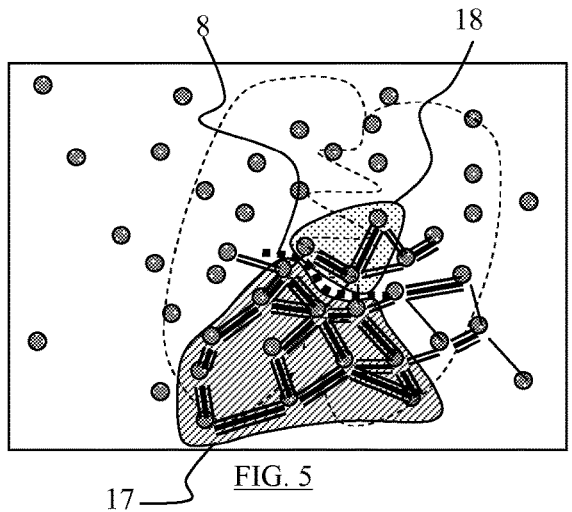

In FIG. 5, a watershed line 8 is identified, i.e. the site where an abrupt fall is noted, a genuine discrepancy between the two groups 17 and 18. This can be represented as a "cliff" which separates two neighbouring groups. This is done by the watershed line technique or by any other technique making it possible to detect two neighbouring groups having the weakest link between them. This cliff corresponds to a low conduction zone.

Figure 6:
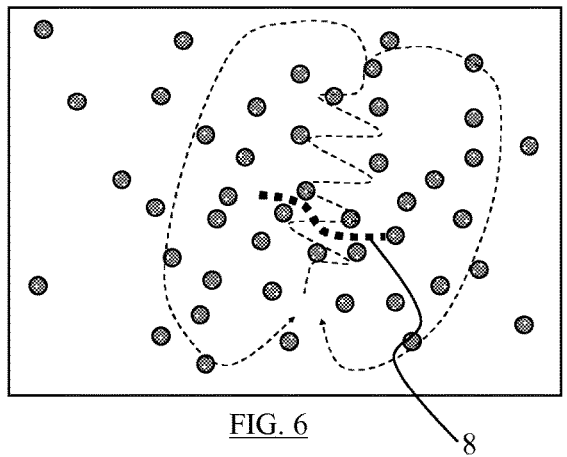
FIG. 6 is a diagrammatic view illustrating the ventricular tachycardia circuit with display of the zone to be ablated across the isthmus.

Ideally, the watershed line 8 is the zone to be burnt away. In FIG. 6, the isthmus is the zone substantially perpendicular to the watershed line 8. The ablation making it possible to interrupt the isthmus can also be carried out at any other site different from the watershed line.

When the stimulated points are not sufficient to correctly calculate the watershed line, other stimulated points are acquired around the indicated zone or zones so as to calculate the watershed line with certainty.

Figure 8:
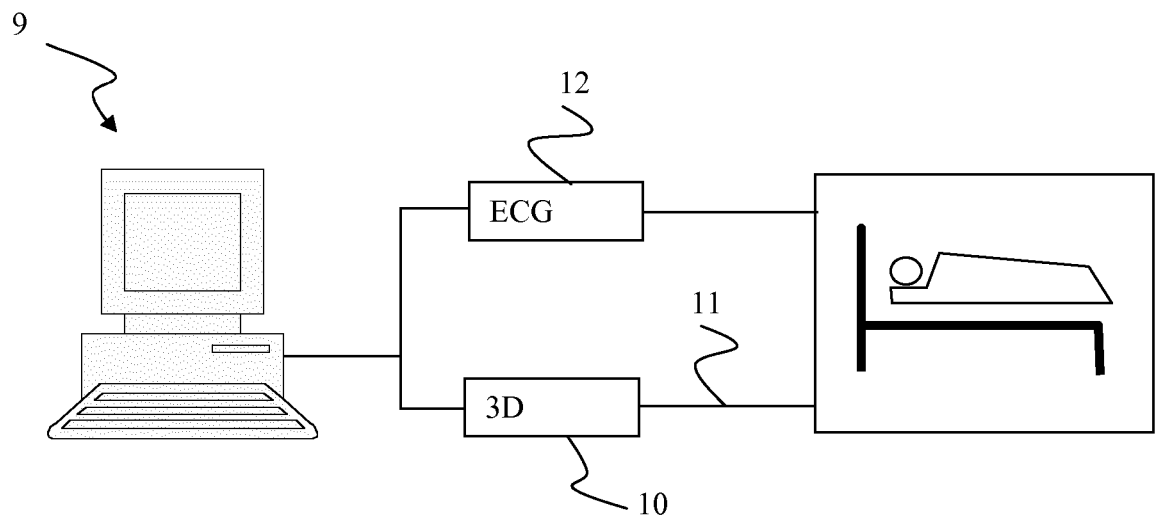
FIG. 8 is a very simplified diagrammatic view of a system for the implementation of the method according to the invention.

FIG. 8 diagrammatically shows a system allowing the present invention to be put into practice. A processing unit 9 can be seen, equipped with at least one microprocessor, memory spaces, communication cards to external peripherals, input/output components and a display means. This processing unit is connected to a mapping device 10 comprising a catheter 11 one end of which can be placed at different sites of the cardiac cavity of a patient. The mapping device 10 is also connected to electrodes (not shown) for producing 3D mappings and thus producing 12-lead ECGs.

The catheter makes it possible to stimulate any point of the cardiac cavity. It also allows radiofrequency ablation to be carried out.

For producing 3D mapping, electromagnetic emission sources are used, placed at the vertices of a triangular frame, itself positioned under the examination table on which the patient is positioned. One of the electromagnetic sensors (the spatial reference) is incorporated in a cutaneous patch positioned under fluoroscopy opposite the cardiac shadow at the level of the patient's back. The other sensor is incorporated at the level of the distal end of the ablation catheter that will be moved to different points at the level of the endocardial surface of the cardiac cavity which will be mapped during the examination. The movement of this catheter can be observed in real time on a monitor. At each new position of the catheter in a given cardiac cavity, this position can be acquired in the form of a point which will appear on the monitor. The points thus acquired will be automatically linked together by the computer program which will create a virtual surface between the different points and, with the accumulation thereof, a three-dimensional geometrical form will be obtained which exactly follow the endocardial contours of the mapped cardiac cavity. The catheter is provided with electrodes making it possible to obtain the bipolar and unipolar endocavitary signal at the level of each of the points which form the virtual reconstruction of the cardiac cavity. It is therefore possible, using a colour coding correlated with the bipolar or unipolar amplitude of the signal obtained, to obtain a mapping of the amplitude of the cardiac cavity examined.

In FIG. 8, an electrophysiology rack 12 allowing the production of the 12-lead ECGs is also shown.

Of course, the invention is not limited to the examples which have just been described and numerous adjustments can be made to these examples without exceeding the scope of the invention. The present invention can consist of a processing unit receiving at the input a 3D mapping of a cardiac cavity, to which optionally, magnetic resonance imaging can be added, as well as sinus rhythm ECGs of a set of stimulated points. The output of the processing unit can be an image of the cardiac cavity on which the watershed line is displayed superimposed. This watershed line can be represented in the form of a set of spatial coordinates which can be used for the ablation.

The method according to the invention advantageously allows identification of the isthmus of a postinfarctal ventricular tachycardia independently of the availability of a 12-lead ECG during ventricular tachycardia. It is henceforth possible to carry out preventive treatments by radiofrequency ablation by means of a catheter for a large number of postinfarctal patients.

The invention claimed is:

1. A method for identifying an isthmus in a three-dimensional mapping of a cardiac cavity from surface electrocardiograms (ECGs), excluding ventricular tachycardia, obtained for each stimulated point of a plurality of stimulated points of the cardiac activity, by a processing unit configured to carry out the following steps:
   a) determining a correlation coefficient for each pair of the stimulated points by comparing the surface electrocardiogram (ECG) associated with each stimulated point of the pair of the stimulated points;
   b) identifying a watershed line based on the correlation coefficients associated with the pair of stimulated points and 3D coordinates of the stimulated points obtained from 3D mapping of the cardiac cavity; and
   c) determining the isthmus in the cardiac cavity that is transverse to the watershed line.

2. The method according to claim 1, further comprising, prior to step a), a step of constituting several volumes which overlap in the 3D mapping of the cardiac cavity, these volumes containing the set of stimulated points, step a) being carried out between stimulated points of each of the volumes.

3. The method according to claim 1, wherein at least one iteration of steps a) and b) is carried out, and wherein at each iteration, new stimulated points are added in the cardiac cavity.

4. The method according to claim 1, wherein the surface electrocardiograms (ECGs) are each a twelve lead surface electrocardiogram (ECG).

5. The method according to claim 4, wherein the correlation coefficient is determined from QRS complexes originating from the twelve lead surface electrocardiograms (ECGs).

6. The method according to claim 5, wherein the correlation coefficient is implemented according to the BARD algorithm called "template matching".

7. The method according to claim 1, wherein step a) further comprises a step for identifying groups of the stimulated points as a function of the level of correlation coefficients between the groups of the stimulated points.

8. The method according to claim 7, wherein the groups of the stimulated points are identified by displaying on a display screen, with an identical color, the stimulated points of the same group.

9. A system for identifying an isthmus in a three-dimensional mapping of a cardiac cavity, the system comprising:
   an electrocardiograph for generating surface electrocardiograms (ECGs), excluding ventricular tachycardia, obtained for each stimulated point of a plurality of stimulated points of the cardiac activity, and
   a processing unit configured to carry out the following steps:
      a) determining a correlation coefficient for each pair of the stimulated points by comparing surface electrocardiogram (ECG) associated with each stimulated point of the pair of the stimulated points;
      b) identifying a watershed line based on the correlation coefficients associated with the pair of the stimulated points and 3D coordinates of the stimulated points obtained from the three-dimensional mapping of the cardiac cavity; and
      c) determining the isthmus in the cardiac cavity that is transverse to the watershed line.

10. The system according to claim 9, further comprising moving an ablation catheter to different points at a level of the endocardial surface of the cardiac cavity.

* * * * *